(12) United States Patent
Mauze et al.

(10) Patent No.: US 6,375,627 B1
(45) Date of Patent: Apr. 23, 2002

(54) PHYSIOLOGICAL FLUID EXTRACTION WITH RAPID ANALYSIS

(75) Inventors: Ganapati R. Mauze, Sunnyvale; Paul Lum, Los Altos; Dominique Freeman, La Honda, all of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/517,711

(22) Filed: Mar. 2, 2000

(51) Int. Cl.$^7$ .................................................. A61B 5/00

(52) U.S. Cl. ....................................... 600/584; 600/309

(58) Field of Search ................................ 600/309, 316, 600/341, 365, 576, 583, 584; 606/181; 422/99; 204/403, 409; 436/68, 164

(56) References Cited

U.S. PATENT DOCUMENTS

| | | | |
|---|---|---|---|
| 5,046,496 A | * 9/1991 | Betts et al. .................. | 600/352 |
| 5,057,277 A | 10/1991 | Mauze et al. .................. | 422/56 |
| 5,080,865 A | * 1/1992 | Leiner et al. ............... | 422/68.1 |
| 5,194,391 A | 3/1993 | Mauze et al. ................ | 436/166 |
| 5,330,634 A | * 7/1994 | Wong et al. ............. | 205/777.5 |
| 5,501,893 A | 3/1996 | Laermer et al. ............. | 428/161 |
| 5,525,518 A | * 6/1996 | Lundsgaard et al. .......... | 436/68 |
| 5,591,139 A | 1/1997 | Lin et al. ..................... | 604/264 |
| 5,700,695 A | * 12/1997 | Yassinzadeh et al. ........ | 436/180 |
| 5,758,643 A | * 6/1998 | Wong et al. ................ | 600/309 |
| 5,855,801 A | 1/1999 | Lin et al. ........................ | 216/2 |
| 5,873,887 A | 2/1999 | King et al. .................. | 606/182 |
| 5,891,053 A | 4/1999 | Sesekura ..................... | 600/583 |
| 6,099,484 A | * 8/2000 | Douglas et al. ............. | 600/583 |

FOREIGN PATENT DOCUMENTS

| | | | |
|---|---|---|---|
| EP | 0317847 A1 | * 11/1988 | .................. 600/576 |

OTHER PUBLICATIONS

Kyle Stanton Lebouitz, "MEMS Microshells for Microneedles, Microscale Fluid Fluid Visualization and Vacuum Packaging of Microdevices"; dissertation submitted in partial satisfaction of the requirements for the degree of Doctor of Philosophy, Fall 1998.

W. Ehrfeld, F. Gotz, D. Munchmeyer, W. Schelb, and D. Schmidt; "Liga Process: Sensor Construction Technique via X–Ray Lithography"; 1998, IEEE.

John I. Peterson, Seth Goldstein, and Raphael V. Fitzgerald; "Fiber optic pH Probe for Phsiological Use", Anal. Chem. 1980, 52, 864–869.

Kenneth E. Bean and Paul S. Gleim, "the Influence of Crystal Orientation on Silicon Semiconductor Processing"; Proceedings of the IEEE, vol. 57, No. 9, Sep. 1969, pp. 1469–1476.

(List continued on next page.)

*Primary Examiner*—Kevin Shaver
*Assistant Examiner*—Charles Marmor, II

(57) ABSTRACT

A device for sampling and analyzing a physiological fluid from the skin of a patient by puncture. The device includes a body and sensors. The body has a needle with a point for puncturing a physiological tissue and a channel in the body for conducting the physiological fluid away from the point. The sensors are located in the body and are accessible to the physiological fluid conducting along the channel for physiological fluid analysis. The device can be used to lance the skin and obtain a representative sample of the physiological fluid, with relatively simple procedures and quick analysis to minimize the exposure of the physiological fluid sample to air.

22 Claims, 5 Drawing Sheets

OTHER PUBLICATIONS

Don L. Kendall, "A New Theory for the anisotropic etching of silicon and some underdeveloped chemical micromachining concepts"; J. Vac. Sci. Technol. A 8(4), Jul./Aug. 1990.

Harry Robbins and Bertram Schwartz, "Chemical Etching of Silicon", Journal of the Electrochemical Society, Jun. 1959, vol. 6, No. 5, pp. 505–508.

Michel J. Declerq, "A New C–Mos Technology Using Anistropic Etching of Silicon", IEEE Journal of Solid–State Circuits, vol. SC–10, No. 4, Aug. 1975.

H. Robbins and B. Schwartz, "Chemical Etching of Silicon, II. The system HF, HN03, H20, and HC2H30", vol. 107, No. 2, Journal of the Electrochemical Society, vol. 107, No. 2.

Kenneth E. Bean, "Anisotropic Etching of Silicon"; IEEE Transactions on Electron Devices, vol. Ed–25, No. 10, Oct. 1978.

Jason Alter, Ph.D, One–Step Separation of Plasma from Whole Blood for in–Vitro Diagnostics; Ginetic Engineering News, vol. 16, No. 5, Mar. 1, 1996.

Graham Davis, "Microfabricated Sensors and the Commercial Development of the i–stat point–of–care system", Chapter 2, pp. 47–76; ISBN 0–471–58505–X, 1998.

* cited by examiner

PHYSIOLOGICAL FLUID EXTRACTION WITH RAPID ANALYSIS

FIELD OF THE INVENTION

The present invention relates to devices for penetrating the skin to extract blood or other fluids for analysis, and more particularly, to a skin-pricking device that is capable of transporting and analyzing physiological fluid from the skin.

BACKGROUND OF THE INVENTION

Medical testing of a patient's body fluid (such as blood) is often required for diagnosis and treatment of diseases. For example, to obtain a blood sample, the current state of-art requires either venipuncture or "finger-stick" using a lancet. Finger-stick tests can be done for measuring blood sugar levels by diabetics using home test kits in "point of care diagnosis." These test kits require that a drop of blood be obtained and placed into a measurement apparatus that calculates and then displays the glucose concentration in the blood sample. To obtain the drop of blood, the user is supplied with a lancet device, which makes a skin prick (typically in the user's finger). The user then "milks" the punctured spot to draw enough blood to the surface of the finger. The blood is then transferred to a test strip placed in the apparatus for measurement. In venipuncture, the blood sample is drawn in a syringe or a vial via a hypodermic needle from a vein and delivered to a measuring apparatus. In both these methods, the blood sample is injected into or applied onto a sensing device, which may be a sensor cartridge, or sensor strip (as in home glucose analysis) or a more sophisticated apparatus as used in laboratory tests. A clear disadvantage of these solutions is that they involve multiple steps, as well as other manipulations by the user. Moreover, in the finger-stick methods, the process of milking and drawing blood sample to the surface leads to changes in the analyte concentration, due to mixing of the sample with interstitial fluid or due to exposure of the sample to the ambient environment (e.g., exposure to air). For these reasons, the current methods of finger-stick sampling cannot be used to measure parameters such as blood gas contents. Due to the low efficiency of transferring the sample to the sensing apparatuses, the two step sampling and sensing methods in venipuncture typically need to draw larger blood samples than are actually required for sensing. Since pain is related to the amount of blood extracted, venipuncture inflicts significant amount of unnecessary pain and trauma to the patient. Thus, there is a need for an apparatus and method for sampling and quickly analyzing blood from a patient with minimal pain using a small volume of sample blood.

SUMMARY OF THE INVENTION

The present invention provides a technique for sampling and analyzing physiological fluid acquired from a tissue on the body of an animal (i.e., physiological tissue or body tissue) such as the skin (e.g., a liquid such as blood from the capillaries beneath the surface of the skin or the interstitial fluid of a tissue). In one aspect, the present invention provides a device for sampling and analyzing a fluid from the physiological tissue (e.g., from capillaries beneath the skin) of a patient by puncture. The device includes a body that includes a needle and sensors. The needle has a point for puncturing the physiological tissue and a channel in the body conducting fluid (e.g., blood) proximally from the wound into the body. Sensors in the body are accessible to blood conducted along the channel for analysis. The device can be used to sample and analyze the fluid quickly, and with minimal exposure to air. In one aspect, the present technique of sampling and analyzing a physiological fluid includes puncturing the physiological tissue with a lancing unit having a channel therein, leading through a needle to a sharp point; conducting the fluid from the physiological tissue from the sharp point up the channel; and analyzing the fluid with sensors along the channel while the fluid is in the channel.

Using the technique of the present invention, a user can conveniently obtain and analyze a small volume of a physiological sample (such as blood) quickly, thereby ensuring that the sample does not have exposure to air. Using a device of the present invention will enable one or more constituents (and parameters) of the patient's physiological fluid to be measured to determine the biochemical parameters (which reflect the patient's physiological condition). Such parameters may include pH, glucose concentration, blood gas content, the concentration of other blood constituents (such as , but not limited to, e.g., creatinine, potassium, chloride, calcium, blood urea nitrogen), and the like. There is no need for the user to undergo extensively invasive procedures such as arterial or venous punctures to measure such parameters, hence making self-monitoring possible for data such as blood gas contents. The convenience afforded by the present invention enables a user to more closely comply with the self-monitoring program prescribed by the health professionals. Further, the device can have a needle that is disposable and well-shielded to prevent exposure of biohazard (such as blood from a sick patient) to others. Additionally, the needle according to the present invention can be mass-produced, thus making such devices more cost-effective and available to users.

DETAILED DESCRIPTION OF THE INVENTION

The present invention involves a technique for a simple and reliable determination of physiological fluid parameters in a less painful way for the patient than current techniques. In one aspect, the present invention employs a physiological fluid sampling device that samples a physiological fluid from the patient and analyzes it substantially immediately, without extensive exposure to air, by utilizing sensors in a channel that receives the physiological fluid during the sampling procedure.

Figure 1:
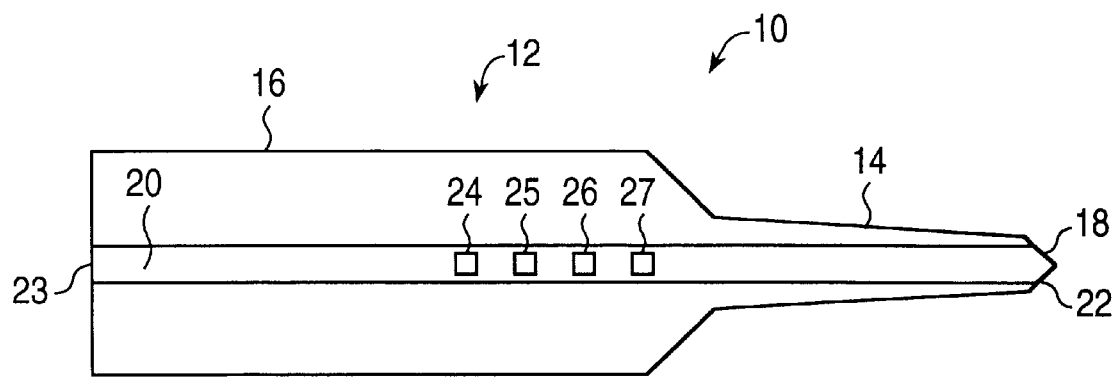
FIG. 1 is a plan view of an embodiment of a sampling needle according to the present invention.
Figure 2:
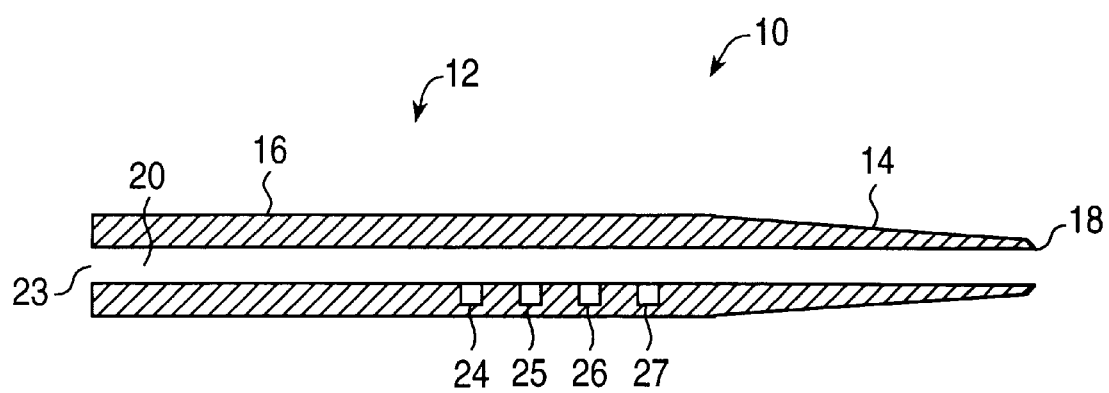
FIG. 2 shows a sectional view of the embodiment of a sampling needle of FIG. 1 according to the present invention.

In one aspect, the present invention provides a sampling needle of which an illustrative embodiment is shown in the plan view in FIG. 1 and the sectional view in FIG. 2. The sampling needle 10 includes a body 12, which has a shaft portion 14 and a plate portion 16. The shaft portion 14 has a distal sharp tip (or point) 18 for puncturing the physiological tissue (or body tissue), such as the skin of an animal. The individual whose physiological tissue is being punctured is herein referred to as the "patient," which can be, for example, a person, a pet, a farm animal, etc. As used herein, the term "distal" refers to the direction towards the patient during the physiological fluid-sampling procedure. The body has a channel 20 which extends from then vicinity of the tip 18 proximally (i.e., the direction away form the tip). The channel 20 has a distal opening 22 from which physiological fluid can enter at its distal end and a proximal opening 23 at its proximal end to provide a stop junction for capillary action. Along the channel 20, preferably on the plate portion 16 are sensors 24, 25, 26, 27 for determining certain parameters (or characteristics) of the physiological fluid, such as pH, concentrations of blood gases, electrolytes, glucose, and the like. Generally, the sampling needle 10 has a shaft of about 1 to 5 mm long with a cross sectional size of about 0.3 mm by 0.3 mm, preferably about 2 mm long with a cross sectional size of about 0.2 mm by 0.2 mm. The channel 20 is generally about 0.1 mm by 0.1 mm, preferably about 0.06 mm by 0.06 mm in cross section. It is to be understood that these dimensions refer to the overall size and do not imply that the needles are necessarily square in cross section. The channel is shaped and sized to facilitate the conduction of the physiological fluid by capillary force and/or by suction.

Figure 3A:
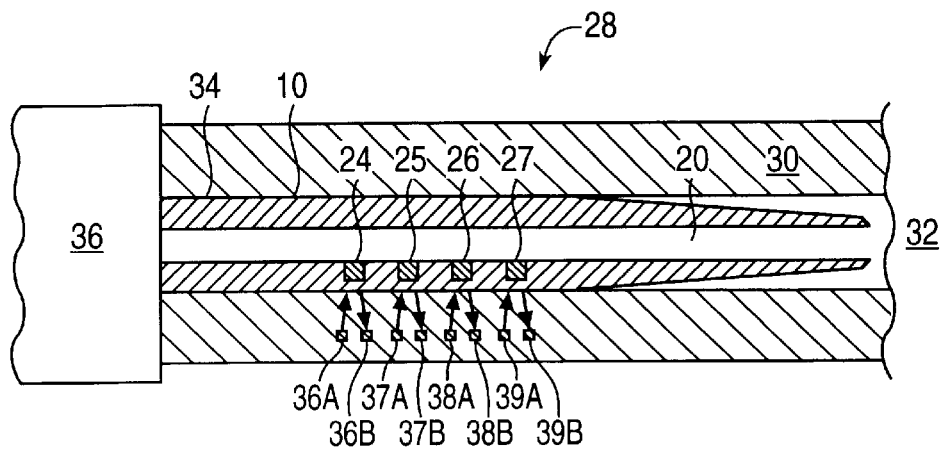
FIG. 3A shows a sectional view in portion of a fluid analyzing apparatus of the present invention.

FIG. 3A shows a sectional view in portion of an embodiment of a device for sampling and analyzing physiological fluid according to the present invention. The physiological fluid analyzer 28 includes the sampling needle 10 of FIG. 1. Further, a shell 30 confines the sampling needle 10 and allows movement only in the proximal-distal directions. When the sampling needle 10 is in its resting position in the shell 30, the distal tip (or point)l 8 is shielded by the shell 30 so that the physiological tissue 32 of the patient or another person will not be inadvertently injured by the distal tip 18 of the sampling needle 10. The proximal end 34 of the sampling needle 10 is secured to a driver (or launcher) 36 (which is schematically shown in portion in FIG. 3A) for driving the sampling needle 10 to skin to sample a physiological fluid (e.g., blood) and for retracting it after sampling the physiological fluid. The shell 30 also contains interrogation elements (or analysis sites) 36A, 36B, 37A, 37B, 38A, 38B, 39A, 39B proximate to the corresponding sensors 24, 25, 26,27 respectively, for sending or receiving signals to the sensors 24–27. In the embodiment shown in FIG. 3A the interrogation elements are optical components for irradiating the sensors 24–27 (namely, 36A, 37A, 38A, 39A) and receiving reflected light therefrom (namely, 36B, 37B, 38B, 39B). The arrows in FIG. 3A indicate light paths for interrogating sensors 24–27. The interrogation elements 36A, 36B, 37A, 37B, 38A, 38B, 39A, 39B are connected to conductors for transmitting current and signals to and/or from the interrogation elements. The conductors for transmitting signals can also be optical fibers for transmitting light. For example, signals can be transmitted from these interrogation elements to a computer, which can either be housed with the driver 36, or at a remote location.

Figure 15:
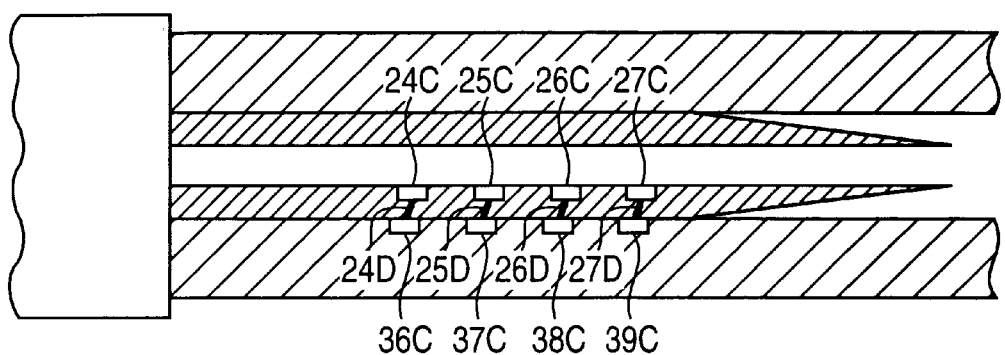
FIG. 15 shows a section view illustrating sensors and interrogating elements of another embodiment of the analyzing apparatus of the present invention.

As shown in FIG. 15, it is to be understood that in other embodiments the interrogation elements 36C, 37C, 38C, 39C can be electrical conductors conveying signals sent from the sensors 24C, 25C, 26C, 27C via electrical conductors 24D, 25D, 26D, 27D. In such cases the sensors corresponding to sensors 24C–27C can contain electrodes that sense analyte concentrations, and the electrodes can have conductors extending to the surface of the plate portion 16 facing the conducting interrogation elements corresponding to interrogation elements 36C–39C.

Figure 3B:
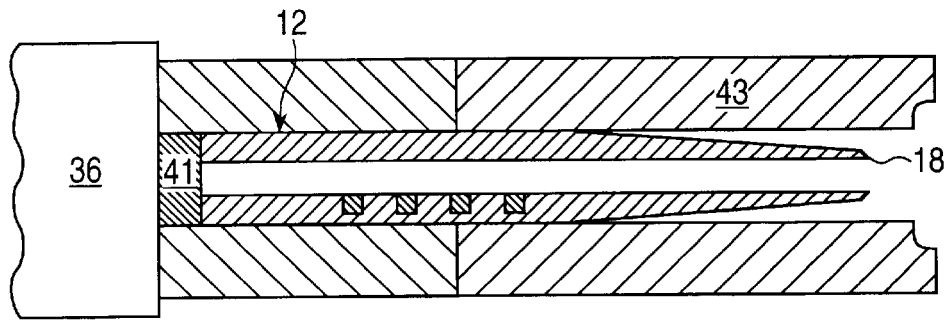
FIG. 3B shows a sectional view in portion of another embodiment of a physiological fluid analyzing apparatus of the present invention.

Many drivers for driving the lancets and needles are known in the art, and a person skilled in the art will be able to adapt them for use as the driver 36 for driving the sampling needle 10. Furthermore, the driver 36 can also have a suction source (not shown in the figures) connected to the proximal opening 24 of the sampling needle 10 for effecting a suction to facilitate the flow of the physiological fluid up the channel 20 from the distal opening 22. One such suction mechanism is described in U.S. Pat. No. 5,891,053 (Sesekura), U.S. Pat. No. 5,873,887 (King et al.) and U.S. Pat. No. 5,666,966 (Horie et al.), which are incorporated by reference in their entireties herein. A filter can also be used to isolate the driver 36 from the sampling needle 12 such that the physiological fluid will not flow past it and contaminate the driver. As shown in FIG. 3B, the filter 41 can be attached to the sampling needle 12 and is disposable. Further, the device can have a disposable cap 43 for shielding the sharp point 18 of the sampling needle 12 for disposal to reduce bio-hazard exposure to a person in the vicinity.

Figure 4:
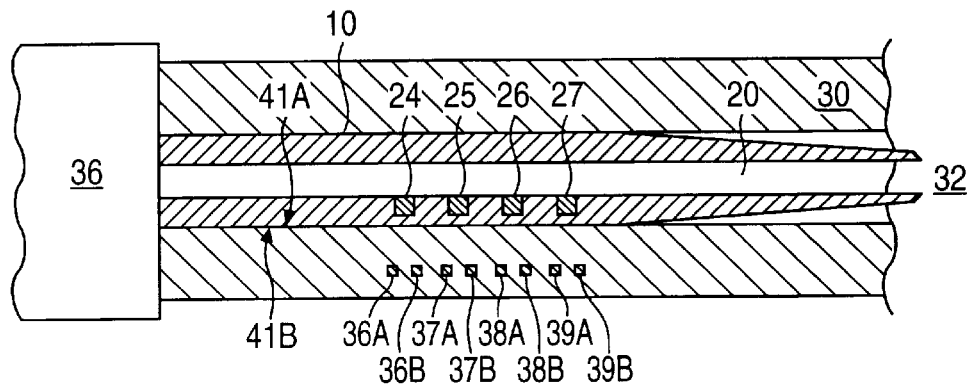
FIG. 4 shows a sectional view in portion of a physiological fluid analyzing apparatus of FIG. 3A with the sampling needle in motion penetrating the physiological tissue of a patient.
Figure 5:
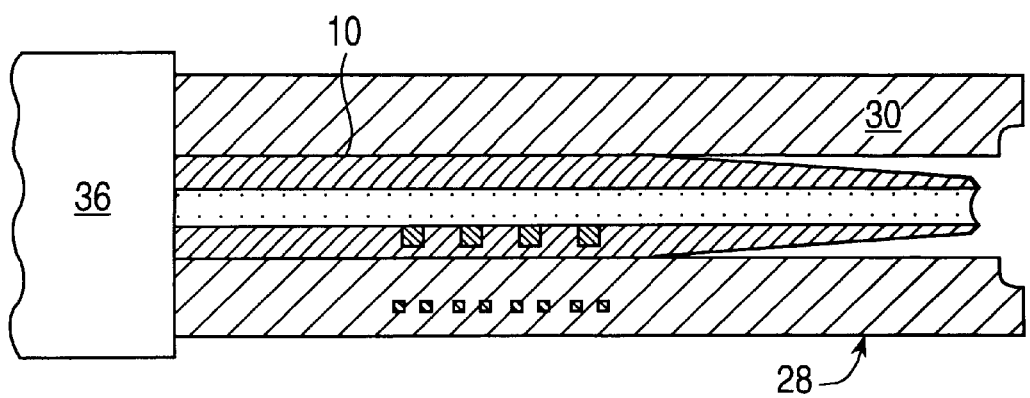
FIG. 5 shows a sectional view in portion of a physiological fluid analyzing apparatus of FIG. 3A after collecting a physiological fluid.

FIG. 4 shows a sectional view in portion of the physiological fluid analyzer 28 when the sampling needle 10 has been driven forward to puncture the physiological tissue (e.g., skin) of the patient. It is noted that when the sampling needle 10 is driven forward (distally) it slides in the distal direction operatively against the shell 30, which confines its freedom of motion in the distal direction when it is driven. It is to be understood that interposing material can be between the shell 30 and the sampling needle, and still allow the sampling needle to move relative to the shell in a translational manner. When the sampling needle 10 is driven distally with the tip 18 extending out of the shell 30, the sensors 24–27 move away from the corresponding interrogation elements 36A, 36B, 37A, 37B, 38A, 38B, 39A, 39B and thus the interrogation elements will not interrogate the sensors 24–27 in this condition. After an adequate amount of the physiological fluid has passed into the sampling needle 10, the sampling needle 10 is retracted back into the shell 30 so that the sharp tip 18 of the sample needle 10 will not be exposed as a bio-hazzard.

The physiological fluid that flows from the body into the channel 20 will quickly pass by the sensors 24–27 and continue on its way towards the proximal opening 23. Since the channel 20 is narrow and only a small volume of air (or gas if the channel has been purposely filled with a storage gas, such as nitrogen before sampling) is in contact with the proximal portion of the physiological fluid passing up the channel 20, the portion of the physiological fluid that eventually settles about the sensors 24–27 when the physiological fluid stops in the channel will not have exposure to air, and thus will have chemistry substantially similar to the physiological fluid in the physiological tissue. In this way, certain parameters of the physiological fluid which may be changed by exposure to air (e.g., gas content of blood) can be sampled and analyzed in vitro, without cumbersome and painful procedures such as inserting a catheter or needle into a vein of a patient.

The physiological fluid is interrogated after the sampling needle 10 is retracted to the position at which the sensors 24–27 are near to and coupled in alignment with their corresponding interrogation elements 36A–39A in the shell 30. The irradiators 36A, 37A, 38A, 39A emit light of the appropriate frequencies into the sensors 24–27 and the light detectors 36B, 37B, 38B, 39B sense the light from the sensors 24–27 to determine the appropriate qualities of interest. Preferably the surface 41A of the body 12 and the surface 41B of the shell 30 where they interface is flat so that light can pass therethrough without much distortion or attenuation. It is noted that a wide variety of irradiators and sensors, as well as techniques of transmission of light or electrical signals are known in the art. Practically any light ranging from x-ray to infra red light can be produced, transmitted to tiny areas, and detected. For example, such light can be transmitted by fiber optics from suitable light sources from a location remote from the shell 30 to the interrogation elements 36A–39A in the shell 30. It is to be understood that the term "remote" includes the situation in which the analyzing electronics are located in the driver 36, or it may be a situation in which the analyzing electronics are off site, as in a different building, etc. Similarly, fiber optics can be used to receive the light from the sensors 24–27, and transmit to a location remote from the shell 30 for analysis. However, light sources and light sensors can be directly positioned at the interrogation elements. Suitable light sources may include light emitting diodes, laser, fluorescent lamp, incandescent lamp, and the like. Filters may be used to select the desirable wavelengths directed to the sensors. If light sources of small sizes are used, they may be positioned at the irradiators 36A, 37A, 38A, 39A If desired, the interrogation elements can be located on the inwardly facing surface of the shell 30 to be as close to the sensors 24–27 as is practical. This arrangement will minimize the intervening space and material through which the light will have to travel and thereby reduce noise. For example, optical fibers can reach all the way to be flush with the inwardly facing surface of the shell 30 near to the sensors 24–27 to transmit light. Further, by minimizing the thickness of the material on the sampling needle 12 that separates the sensors 24–27 from the shell 30, the efficiency of transmission of signals or light between the interrogation elements and the sensors 24–27 can be increased.

It is to be understood that one or more of the sensors 24–27 can contain an electrode for measuring analyte electrochemistry (e.g., pH, conductivity, etc.). Such electrodes will not be interrogated by optical means. Rather, electrical leads will lead from the sensors 24–27 through the interrogation elements similar to elements 36A–39B. Such leads can lead to analyzers remote from the shell 30.

The sampling needle 10 can be made with silicon integrated circuit (IC) techniques using wet and dry etching. Techniques for adapting IC technology for making needles can be found, for example, in Kyle Lebouitz, Ph.D. dissertation entitled "MEMS Microshells for Microneedles, Microscale Fluid Visualization, and Vacuum Packaging of Microdevices," University of California at Berkeley, 1998; U.S. Pat. No. 5,855,801 (Lin et al.), and U.S. Pat. No. 5,591,139 (Lin et al.), which are incorporated by reference in their entireties herein. The IC techniques take advantage of the fact that silicon can be etched isotropically and anisotropically by using different etchant chemicals, thereby producing channels of different shapes and angles. Techniques of isotropic as well as anisotropic etching of silicon are known in the art, e.g., Kenneth E. Bean, "Anisotropic etching of silicon," *IEEE Trans. On Electron Devices*, Vol ED-25, No. 10, p. 1185–1193, Oct. 1978; Kenneth E. Bean et al., "The influence of crystal orientation on silicon semiconductor processing," *Proceedings of the IEEE*, Vol 57, No. 9, p. 1469–1476, September 1969; Don L. Kendall, "A new theory for the anisotropic etching of silicon and some underdeveloped chemical micromachining concepts, *J. Vac. Sci. Technolo. A.*, 8(4), p. 3598–3605, Jul./Aug. 1990; Michel J. Declercq, "A new C-MOS technology using anisotropic etching of silicon," *IEEE J. of Solid state Circuits*, Vol. SC-10, No. 4, p. 191–196, August 1975; Harry Robbins et al., "Chemical etching of silicon, I", *J. of the Electrochemical Society*, p. 505–508, June 1959; and Harry Robbins et al., "Chemical etching of silicon, II.", *J. of the Electrochemical Society*, Vol. 107, No. 2, p. 108–111, Februry 1960. Isotropic etchants, such as hydrofluoric acid, nitric acid, acetic acid, and the like, etch silicon in all crystalographic direction at the same rate.

Figure 6:
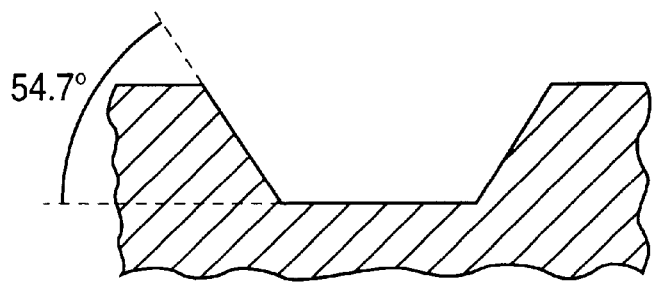
FIG. 6 and FIG. 7 show sectional views illustrating anisotropic etching of silicon.
Figure 7:
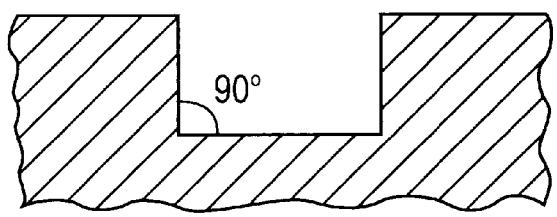
Figure 8:
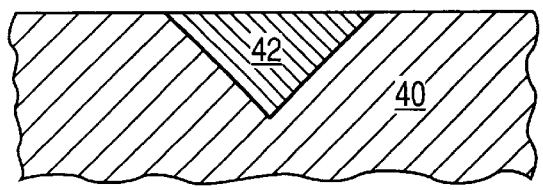
FIG. 8 to 12 show sectional views illustrating the process in forming a channel in a sampling needle according to the present invention.

On the other hand, anisotropic etchants, such as potassium hydroxide, hydrazine, ethylene-diamine (EDA), and the like, etch the (100) plane of the silicon crystal at a much higher rate than (111) planes. Using isotropic and anisotropic techniques, one can etch silicon to obtain the sampling needles of the present invention. For example, a trough-shaped channel with 54.7° side-wall (see FIG. 6) can be etched with KOH. Also, a trough-shaped channel with 90° side wall (see FIG. 7) can be made using the STS Bosch process. See U.S. Pat. No. 5,501,893, which is incorporated by reference in its entirety herein. The Bosch Process is a plasma etch process developed by Robert Bosch GmbH and is a known process for deep well etching. It implements concurrent and/or iterative deposition and etching chemistries and allows the engineering of sidewall passivation in accordance with the aspect ratio needed, the open area of silicon (load), and the use or nonuse of buried oxide as an etch stop. The current Bosch process uses an inductively coupled high density plasma source and fluorine etching species. The high density of neutral fluorine etching species ensures that mass transport within the plasma is diffusion dominated.

Furthermore, it is commonly known that glass and $SiO_2$ can be etched with suitable chemicals, e.g., buffered hydrofluoric acid (HF) mixtures; glass, $SiO_2$, polysilicon. Silicon nitride can be dry-etched with plasma chemistry. Silicon nitride can also be wet-etched with phosphoric acid ($H_3PO_4$).

Briefly, FIG. 8 to FIG. 12 illustrate in sectional views how a sampling needle with a channel can be made. These figures correspond to the plate portion of the sampling needle. However, a person skilled in the art will know that shaft portion of the sampling needle can be fashioned using substantially similar techniques. A silicon substrate 40 is etched anisotropically to form a trough, which is filled with $SiO_2$ 42, eventually resulting in a structure seen in FIG. 8. The top of the $SiO_2$ 42 and the substrate 40 are flush, which can be accomplished by milling off any excessive substrate or $SiO_2$ material. A layer of phosphosilicate glass (PSG) 44 can be laid on the $SiO_2$ 42 extending slightly wider than and covering the $SiO_2$ material 42. Thus the phosphosilicate glass 44 and the substrate 40 encircles the $SiO_2$ material 42.

Figure 9:
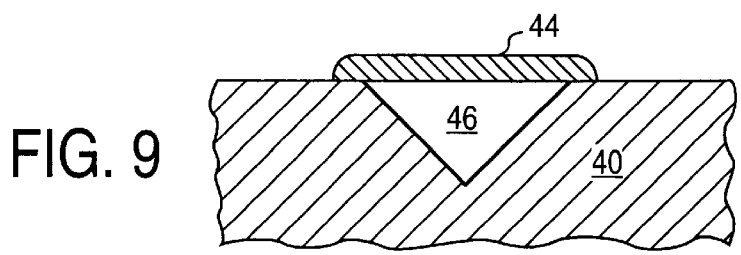
Figure 10:
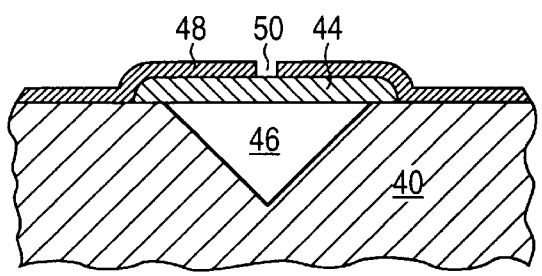

As shown in FIG. 9, the $SiO_2$ 42 material then can be etched away forming a channel 46. A layer of silicon nitride $Si_3N_4$ 48 can then be laid on the substrate 40 and the PSG, except in certain areas where opening 50 are left unoccupied by $Si_3N_4$, see FIG. 10. The openings 50 are for providing access to etchants to etch away the PSG 44, thus leaving a sampling channel 52. More $Si_3N_4$ can be laid on the $Si_3N_4$ layer 48 to make the resulting $Si_3N_4$ layer 54 substantially flat to facilitate sliding against a surface. Openings 50 are left for introducing sensing chemicals for access by the physiological fluid that will flow past in the sampling channel 52.

Figure 11:
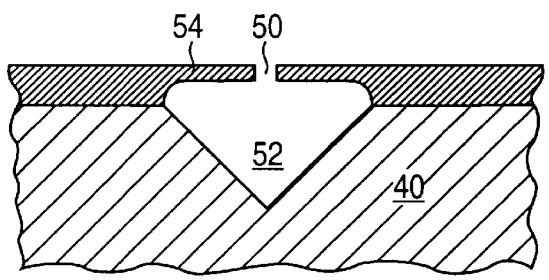
Figure 12:
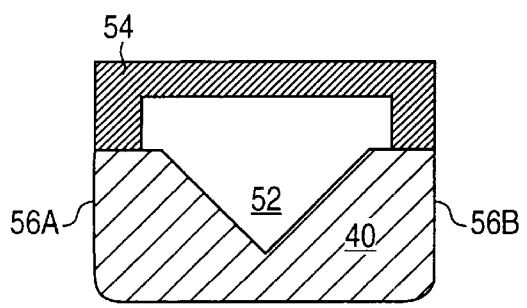

FIG. 11 shows the sectional view of the plate portion of a sampling needle. Similarly, the shaft portion of the sampling needle can have a section view similar to that in FIG. 12, in which the sampling channel 52 is bounded by the substrate 40 and the $Si_3N_4$ layer 54. The side edges 56A, 56B of the silicon substrate layer 40 in the shaft portion can be formed by anisotropic etching. It is preferred that openings 50 be absent in the shaft portion to maintain the shaft stiffness to facilitate penetration into the physiological tissue of a patient. The top cover of the channel is made from silicon nitride. Polysilicon may also be used for making the cover. With anisotropic etching, the needle can have a cross-section that has stright sides (e.g., side edges 56A, 56B). It is noted that one skilled in the art can make a needle with sides that are not necessarily parallel in its cross section.

As previously mentioned, the sensors 24–27 may have electrodes or chemicals immobilized therein for sensing various parameters of the physiological fluid. For illustrative purposes, sensors that can optically interrogated are described. However, viewing the present disclosure, a person skilled in the art will understand that other sensors and methods of interrogation and signal communication can be used. Illustrative examples of sensors are described below.

pH Sensors

Optical pH sensors can be based on light absorbance or fluorescence changes of a weakly dissociating dye in response to changes in pH. A weakly dissociating dye HA (in acid form) in solution is in equilibrium with its base form $A^-$ according to the equation $$HA \leftrightarrows A^- + H^+ \qquad \text{Eq. S1.}$$

With brackets indicating the concentration of a substance, let $[A^-]$ be the concentration of $A^-$, $[H^+]$ be the concentration of $H^+$, and $[HA]$ be the concentration of HA, the equilibrium constant Ka for this reaction is $$Ka=[A^-][H^+]/[HA] \qquad \text{Eq. S2.}$$

Since $pH=-\log [H^+]$ and $pKa=-\log Ka$, $$pH=pKa-\log [HA]/[A^-] \qquad \text{Eq. S3.}$$

In a sensor in which a fixed amount of the dye is C, which may be the case if the dye is immobilized in a matrix, in the absence of bleaching and other losses of the dye, C remains constant and

$$C=[HA]+[A^-] \qquad \text{Eq. S4.}$$

This leads to the following:

$$pH=pKa+\log\{C/[HA]-1\} \qquad \text{Eq. S5.}$$

Thus, the pH can be measured by measuring the concentration of either form of the dye, i.e., [HA] or [$A^-$].

In some pH sensitive dyes, such as phenol red, the acid form and the base form absorb radiation in the different spectral regions. Thus, for phenol red the acid form has an absorption peak at about 430 nm and the base form has an absorption peak at about 550 nm. According to the Beer-Lambert Law:

$$\text{Absorbance }[A^-]=\epsilon L[A^-]=\log Io/I \qquad \text{Eq. S6.}$$

where $\epsilon$ is the molar extinction coefficient of $A^-$, L is the length of the path traveled by the light, and Io and I are the intensities of the transmitted light when $A^-$ is absent and present, respectively.

Combining Eq. S5 and Eq. S6, one arrives at:

$$pH=pKa-\log\{C\epsilon L/\log(Io/I)-1\} \qquad \text{Eq. S7.}$$

Eq. S7 yields an S shaped curve relating pH to the ratio of intensities (Io/I).

In fluorescent dyes such as HPTS (8-hydroxy-1,3,6-pyrenetrisulfonic acid), the energy absorbed by HA and $A^-$ (at about 405 nm and about 470 nm respectively) is emitted as fluorescence at about 520 nm. The relationship between fluorescence intensity, $I_F$, emitted by a sample containing fluorophore concentration C with extinction coefficient E and fluorescence quantum yield $\Phi$ (the ratio of the number of photons emitted to the number absorbed) is

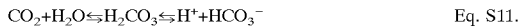

$$I_F=Io\Phi\eta\{1-\exp(-\epsilon LC)\} \qquad \text{Eq. S8.}$$

where $\eta$ is the optical collection efficiency of the instrument.

At low absorbance, this equation can be simplified to $$I_F=2.3Io\Phi\eta\epsilon LC \qquad \text{Eq. S9.}$$

For a pH sensitive fluorescent dye excited at the absorption peak of the base form the fluorescent intensity, $I_{FA}$ is related to pH by:

$$pH=pKa-\log\{\text{constant}/I_{FA}-1\} \qquad \text{Eq. S10.}$$

An equation for the acid form of the dye can be derived in a similar way.

$PCO_2$ Sensors

Partial pressure of carbon dioxide, $PCO_2$, is usually measured using the Severinghaus Principle, as shown below. $CO_2$ dissolved in water dissociates to form hydrogen ions ($H^+$) and bicarbonate ions ($HCO_3^-$).

$$CO_2+H_2O\leftrightarrows H_2CO_3\leftrightarrows H^++HCO_3^- \qquad \text{Eq. S11.}$$

At equilibrium the dissolved concentration of $CO_2$ in an aqueous sample such as blood is proportional to the partial pressure of $CO_2$. The equilibrium constant (dissociation constant) for $CO_2$ in water is $$K_{CO2}=\{[H^+][HCO_3^-]\}/\{[CO_2][H_2O]\} \qquad \text{Eq. S12.}$$

If the medium in which the measurement is made is an aqueous solution of $NaHCO_3$, which dissociates completely into $Na^+$ and $HCO_3^-$ ions, the total concentrations of $HCO_3^-$ and $H_2O$ in the medium remain fairly constant and Eq. S12 can be shown to lead to $$PCO_2=\text{constantA}[H^+] \text{ or } pH=\text{constantB}+\log PCO_2 \qquad \text{Eq. S13.}$$

The above equation indicates that $CO_2$ dissolved in a sample can be measured by measuring the pH of a bicarbonate solution in equilibrium with the sample. To avoid changes in the sample pH from affecting the $CO_2$ measurements, the sensor with the bicarbonate solution and a pH sensitive dye for optical sensing can be encapsulated in a or membrane that allows only $CO_2$ to equilibrate with the buffer solution. Such a membrane acts as a barrier to the hydrogen ions in the test sample.

$PO_2$ Sensors

Oxygen is an excellent quencher of fluorescence of many fluorophores. Optical techniques for oxygen sensing can be based on fluorescence quenching of an excited state of a dye (fluorophore) molecule. The excitation of a fluorophore F and its quenching by an oxygen molecule is represented by the following equations:

$$F + h\nu_{ex} \rightarrow F^* \quad \text{Eq. S14.}$$

where h is Planck's constant, $\nu_{ex}$ is the excitation frequency of the radiation and * represent the excited state of a substance.

For radiative decay, $$F^* \rightarrow F + h\nu_{em} \quad \text{Eq. S15.}$$

where $\nu_{em}$ is the frequency of the radiation emitted at the decay of F*.

For nonradiative decay, $$F^* \rightarrow F + \Delta H \quad \text{Eq. S16.}$$

where $\Delta H$ is the change in enthalpy. When the fluorescence is quenched by collision with oxygen molecules, we have $$F^* + \tfrac{1}{2} O_2 \rightarrow F + O^* \quad \text{Eq. S17.}$$

and $$O^* \rightarrow \tfrac{1}{2} O_2 + \Delta H \quad \text{Eq. S18.}$$

Thus, the amount of oxygen present can be determined by measuring the oxygen quenching of an excited form of the fluorophore.

The rate of decay of an excited fluorophore F* after instantaneous excitation is $$d/dt[F^*]_o = -(\gamma + \kappa)[F^*]_o \quad \text{Eq. S19.}$$

where $\gamma$ and $\kappa$ are rate constants for radiative and nonradiative decays (i.e., without quencher). Under continuous illumination a constant population of the excited fluorophores, i.e., F*, is established.

In the absence of a quencher (represented by a suffix "o")

$$d/dt[F^*]_o = f(t) - (\gamma + \kappa)[F^*]_o = 0 \quad \text{Eq. S20.}$$

where f(t) is the constant excitation function.

With the presence of a quencher, the equation becomes:

$$d/dt[F^*] = f(t) - \{(\gamma + \kappa) + k_q[Q]\}[F^*] = 0 \quad \text{Eq. S21.}$$

where $k_q$ is the rate constant of the reaction represented by Eq. S17 (rate of quenching) and [Q] is the concentration of the quencher (O$_2$). Eliminating f(t) and writing $(\gamma+\kappa)$ as $1/\tau_o$, where $\tau_o$ is the lifetime of the fluorophore in the absence of a quencher, the result is:

$$[F^*]_o/[F^*] = 1 + k_q \quad \text{Eq. S22.}$$

Assuming the rate of nonradiative decay does not change in the presence of quencher and that the intensity of fluorescence is proportional to the number of radiating fluorophores, the equation can be written as:

$$I_{Fo}/I_F = 1 + K_{sv}[Q] \quad \text{Eq. S23.}$$

where $K_{sv}$ equals $k_q \tau_o$ and is known as the Stem-Volmer constant and Eq. S22 and Eq. S23 are variations of the Stem-Volmer equation. Thus, by measuring the intensity of the fluorescence emission by a continuously excited fluorophore the concentration of the quencher such as oxygen can be measured using the Stem-Volmer equation.

For lifetime measurements the fluorophore can be excited by a delta function and the rate of fluorescence decay is observed. According to Eq. S20 the lifetime of the fluoresce decay in the absence of fluorophore is $$\tau_o = 1/(\gamma + \kappa) \quad \text{Eq. S24.}$$

In the presence of a quencher, the lifetime is $$\tau = 1/(1/\tau_o + k_q[Q]) \quad \text{Eq. S25.}$$

and $$\tau_o/\tau = 1 + K_{sv}[Q] \quad \text{Eq. S26.}$$

which is the lifetime form of the Stem-Volmer Equation and can be used to determine oxygen concentration using lifetime measurements.

Electrolyte Sensors

Cations such as Na$^+$, K$^+$, Ca$^{++}$, and Mg$^{++}$ can be measured optically on very similar principles. Typically one selects an ion selective ionophore. Such ionophores are lipophillic inclusion compounds which typically have a ring-like structure. In such a compound, the ring has several slightly electronegative atoms such as oxygen in it. The size of the ring and the total number of the oxygen atoms determine the relative preference (selectivity) of the ionophore to the cations of various sizes and charged states. Another class of ionophore undergo conformational changes upon selective binding of a cation. Thus a double crown ether based ionophore called BME-44 forms a clam shell like enclosure for an included potassium ion. BME-44 has two crown ethers connected by a 3 carbon chain. When a potassium ion is present, the two crown ethers fold over to form the clam shell.

These ionophores are lipophillic and are sequestered in a hydrophobic polymer such as polyvinylchloride (PVC) along with a large amount of plasticizer. The ionophores extract the selective ion from the aqueous solution in contact with the polymer surface. Because the ion finds itself in a more favorable energy environment in the ionophore than in the aqueous surrounding, it readily enters the hydrophobic phase of the polymer. However, this causes a charge imbalance in the polymer phase and at the surface of the polymer. The excess charge build-up in the polymer can be used to expel another less favored cation such as H$^+$ from the polymer phase. Alternatively, a charged double layer is formed at the surface of the polymer. The number of cations expelled or the potential gradient at the surface is proportional to the concentration of the cation in the aqueous solution. Similar ionophores are also available for some anions such as chloride ions. Extraction of an anion into the polymer phase will cause another anion to be expelled or a cation such as an hydrogen ion to accompany the anion into the polymer phase.

The potential build up at the surface of the polymer can be measured optically using potential sensitive dyes. The fluoresce of some dyes, such as rhodamine B, is a strong function of the electrical charge in its vicinity. Thus, measurement of the fluorescence changes of a polymer film in which such a dye is immobilized along with an ionophore can be used to measure the concentration of the selective ion in a sample.

As mentioned above, extraction of a positive ion into a hydrophobic polymer by an ionophore can be made to expel another cation such as an hydrogen ion. Thus, if a pH sensitive dye such as HPTS of phenol red or bromothymol blue is located within the polymer, the dye will lose an hydrogen ion when a cation is extracted from the sample by the ionophore. Thus the optical absorption or the fluorescence emission of the dye will change as in the pH sensors described above. Reverse of this effect can be used to determine the concentration of anions.

The folding of BME-44 in the presence of potassium ion can be made to bring a fluorophore such as rhodamine and a quencher such as fluorescein closer together. In this configuration the Foerster energy transfer from the fluorophore to the quencher causes the change in fluorescence in proportion to the number of potassium ions extracted. When an electron donor is placed between a fluorophore and an ionophore (for cations), the ability of the donor to transfer an electron to the excited fluorophore is blocked when a cation is located in the ionophore. Thus when there is no cation in the ionophore, the fluorescence process is nonradiative. When a cation is captured by the ionophore, the electron transfer to the fluorophore is blocked and the fluorescence energy is radiatively emitted.

Metabolite sensors

Metabolites such as glucose, lactate and creatinine are measured using enzymatic conversion of these species (substrates) into another molecule such as hydrogen peroxide. Alternatively, the enzymatic conversion of the substrates is accompanied by consumption of another species such as oxygen. Thus sensor measuring the concentration of any of these generated or consumed species can be used to determine the concentration of the substrate.

Glucose is converted into hydrogen peroxide while consuming oxygen by glucose oxidase (GOD) according to the following equation:

$$Glucose + GOD + O_2 \rightarrow gluconic\ acid + H_2O_2 \qquad Eq.\ S27.$$

Lactate is converted into pyruvate catalyzed by lactate dehydrogenase and mediated by NAD generating hydrogen ions:

$$Lactate + NAD \rightarrow Pyruvate + NADH + H^+ \qquad Eq.\ S28.$$

Creatinine can be measured using a multienzyme assay involving the following reactions:

$$Creatinine + H_2O \rightarrow Creatine\ (enzyme:\ Creatinine\ Amidohydrolase) \qquad Eq.\ S29.$$

$$Creatine \rightarrow Sarcosine + Urea\ (enzyme:\ Creatine\ Amidinohydrolase) \qquad Eq.\ S30.$$

$$Sarcosine + H_2O + O_2 \rightarrow Glycine + HCHO + H_2O_2 (enzyme:\ Sarcosine\ Oxidase) \qquad Eq.\ S31.$$

Equations S27 through S31 indicate that glucose and creatinine can be measured using oxygen sensing methods discussed above. However, the oxygen tension in a sample like blood can vary considerably. It is therefore preferred to make this reaction oxygen independent. In glucose sensing this is achieved by using a mediator such as ferricyanide which replaces oxygen. For measuring lactate, a pH sensor can be used. Here a change in pH of the sample will also affect the measurements of lactate. In these situations it is necessary to measure the $PO_2$ and pH of the sample and correct for the interferences.

Figure 13:
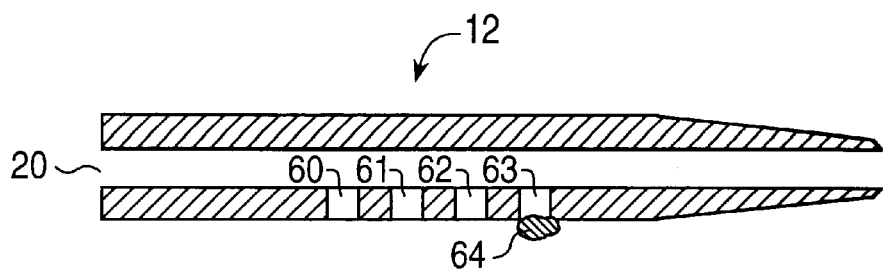
FIG. 13 shows a sectional view illustrating the formation of sensors in the sampling needle.
Figure 14:
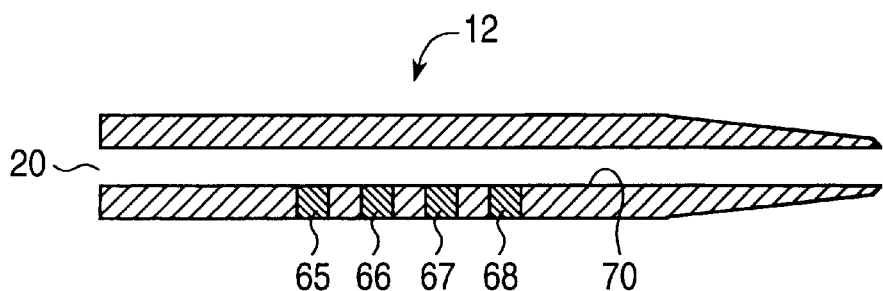
FIG. 14 shows a sectional view illustrating sensors after being formed in the sampling needle.

Sensor chemicals for interacting with the particular constituents of interest (e.g., glucose, oxygen, hydrogen ions, metabolites, etc.) in the physiological fluid for sensing such constituents can be immobilized in the sampling needle such as the one shown in FIG. 1. and FIG. 2. As shown in the illustrative embodiment in FIG. 13, one method is to form a sampling needle with holes 60, 61, 62, 63 extending through the body 12 from an external space to the channel 20 and then placing a small amount of a liquid or a solution of polymer precursor (which contains appropriate sensor chemicals), such as polymer precursor liquid 64, into each hole. The small dimensions of the holes 60, 61, 62, 63 will facilitate wicking the liquid into the holes by capillary force. The polymer precursor can then be solidified, which can be accomplished by radiation (e.g., ultraviolet light), heat, catalyst, etc., forming a sampling needle shown in FIG. 14, having sensors 65, 66, 67, 68.

Although it is usually convenient to use liquids or solutions to form the sensors in these holes, it is also possible to place solid or semisolid materials to form the sensors. It is to be understood that the sensors thus made can be flush with the Luminal wall 70, extending slightly into the channel 20 from the Luminal wall 70, or in the form of a depression (or cavity). Further, more than one layer of materials can be placed into the holes 60, 61, 62, 63, thereby immobilizing different chemicals or forming barriers to inhibit diffusion of different chemicals at different rates. Examples of materials that can be used to form the sensors, e.g., by light sensitive cross-linking polymerization to induce solidification, are known in the art. For example, a solution of acrylamide monomers, a cross linker such as methylene bisacrylamide, an initiator and an indicator such as phenol red can be placed in these holes. Polymerization can be allowed to occur and thus forming a hydrogel of polyacrylamide with phenol red immobilized therein. Such a hydrogel can be used as a pH sensor based on optical absorption measurement of phenol red. The details of the chemical composition of materials to form such a sensor are available in the literature, e.g., Peterson, J. I., Goldstein, S. R., Fitzgerald, R. V., and Buckold, D. K., Fiberoptic pH probe for physiological use, *Anal. Chem.*, 52, pp 864–869 (1980). Methods of making oxygen sensor materials can be found in U.S. Pat. No. 5, 057,277 and U.S. Pat. No. 5,194,391, which are incorporated by reference in their entireties herein. Such materials can be placed in the devices of the present invention.

The sampling needles of the present invention can be made directly by etch processing of silicon. Alternatively, the sampling needles can be made by making a master mold by etching processes and then by molding from the master mold. A similar technique using high aspect ratio photoresist patterns through the LIGA process can be used. A combination of seed metal deposition followed by electroplating to form a metallized structure is followed by the complete removal of the photoresist pattern. Similar processes have been described in the literature, both using and not using the LIGA process. The LIGA process can be further referenced from "LIGA Process: Sensor Construction Techniques via X-Ray Lithography," Technical Digest, IEEE Solid-State Sensor and Actuator Workshop, Hilton Head Island, SC, Jun. 6–9, 1988, pp 1–4. After the photoresist pattern has been removed, the remaining metallic shell becomes the hollow channel with holes, the exception being that this structure is made from metallic material such as nickel rather than silicon, polysilicon, silicon nitride, and the like.

Such a process can be described by the following steps. If a side of a planar hollow needle is defined initially on a planar silicon substrate, this definition is preferably by a photolithographic process. A thin layer of conductive seed metal, such as about 500 Angstroms typically, of sputtered Nickel is deposited on a about 3000 Angstroms typically, thin oxide coated silicon wafer. A negative photoresist pattern of a planar needle is deposited and aligned on the thin oxide silicon wafer. This very thick photoresist in the range about 10 microns to 1000 microns typically, is processed with the LIGA procedure known to those in the art.

The developed resist cavities form metal seed areas for electrodepositing a thick Nickel layer in the range about 0.1 to 0.25 mm thick. With this metal pattern defining a planar needle completed, a very thick layer of photoresist preferably in the range about 10 microns to 1000 microns thick typically, is deposited on the planar surface electrodeposited Nickel and remaining photoresist. A pattern resembling the inner core of the planar needle is aligned and developed on top of the previously defined planar needle side pattern.

The photolithographic process can be done by the method of LIGA. The core of the planar needle would be remaining after respective wet development of the LIGA processed photoresist. This very thick wet resist processing is known to those in the art. Subsequently a conductive seed metal is used to coat both the sides and the top of the remaining photoresist resembling the planar needle core. A follow-up photoresist pattern will be aligned and developed to coat areas where electrodeposition of the remaining planar needle will not occur. This mask pattern will define the remaining planar needles sides and top. The entire silicon substrate is again placed within an electrodeposition bath and the thick metal allowed to grow to thicknesses resembling its first thick metal layer. After the thick metal electrodeposition has completed, all of the photoresist can be removed with solvents and plasma etching. These methodologies are well known to those in the art. A thick hollow structure fabricated with nickel metal will remain along with a very thin web of Nickel connecting all the planar needles. The nickel metal patterns being the hollow planar needles on the silicon wafer can be individually separated by a short wet acid nickel etch to removed the thin nickel webbing. An option may be to not remove this webbing and to remove the entire metal structure from the silicon wafer by dissolving the thin oxide layer between the nickel pattern and the silicon wafer. The individual planar needles can be separated after further needle coatings or added processing for the respective usage application.

The fabrication of sensor holes on the top or bottom sides of the hollow planar needle can be easily patterned and processed during the photolithographic steps defining the initial bottom layer or final top mask definition, respectively. Areas where there should be sensor or port holes will contain photoresist inhibiting thick nickel layer electrodeposition.

Although the preferred embodiment of the present invention has been described in detail, it is to be understood that the present invention can be modified by one skilled in the art, especially in size and shape, and still remain within the scope of the present invention.

What is claimed is:

1. A device for analyzing a physiological fluid from a physiological tissue comprising:
    (a) a body, including a needle with a point for puncturing a physiological tissue and a channel in the body for conducting a physiological fluid extracted from the physiological tissue proximally from the point;
    (b) sensors in the body, wherein the sensors are proximate the point of the needle and accessible to the physiological fluid conducting along the channel for analyzing the physiological fluid; and
    (c) interrogation elements corresponding to the sensors in the body for obtaining information from the sensors, said interrogation elements in communication with an analyzer.

2. A device according to claim 1 further comprising a shell having the interrogation elements.

3. A device according to claim 2 wherein the needle has a cross section that includes straight sides.

4. A device according to claim 2 wherein the body is detachable from the shell to be replaced with a new body.

5. A device according to claim 2 wherein one or more of the sensors each have a recess in the channel, said recesses containing chemicals that interact with specific constituents of the physiological fluid for sensing characteristics thereof.

6. A device according to claim 2 wherein at least one of the sensors has no fluid communication with any space external to the body except through the channel and contains a chemical that reacts with a constituent of the physiological fluid.

7. A device according to claim 2 wherein the body has two halves, at least one of which has a groove such that the two halves can be coupled for the groove on a half in conjunction with the other half to form the channel.

8. A device according to claim 2 wherein the body is slidable on the shell for positioning the sensors in the body to be proximate to the interrogation elements for obtaining information from the sensors.

9. A device according to claim 8 further comprising a suction source connected to the channel for facilitating conduction of the physiological fluid from the point to the sensors.

10. A device according to claim 2 further comprising a chemical that reacts with an analyte in the physiological fluid in one of the sensors.

11. A device according to claim 2 wherein the body has a portion that has a planar surface through which light can penetrate to interrogate the physiological fluid in at least one of the sensors.

12. A device according to claim 2 wherein at least one of the interrogation elements includes electrical contact to contact an electrical conductor on the body to conduct electrical signals from the sensor corresponding to the interrogation element.

13. A device according to claim 2 wherein the body has a layer of material on its outer surface extending substantially from the point of the needle to an end in the body away from the point.

14. A method for analyzing a physiological fluid from a physiological tissue, comprising:
    (a) puncturing the physiological tissue with a lancing unit having a needle with a sharp point and a channel leading from the sharp point to a portion of the lancing unit distant from the sharp point, said needle comprising sensors adjacent said channel wherein said sensors are in communication with interrogation elements in communication with an analyzer;
    (b) conducting a physiological fluid from the physiological tissue from the sharp point up the channel past said sensors; and
    (c) directly analyzing the physiological fluid while the physiological fluid is in the channel employing said interrogation elements in communication with said analyzer.

15. A method according to claim 14 further comprising analyzing the physiological fluid with sensors having chemicals that changes a characteristic in the presence of a constituent in the physiological fluid.

16. A method according to claim 14 further comprising moving the lancing unit after the physiological fluid has conducted up the channel to locate the sensors near to interrogation elements in a shell surrounding the lancing unit to provide information on the physiological fluid to the shell from the sensors.

17. A method according to claim 16 further comprising optically interrogating the sensors at the interrogation elements.

18. A method according to claim 16 further comprising receiving electrical signals from at least one of the sensors by one of the interrogation elements.

19. A method according to claim 16 further comprising installing a lancing unit into the shell such that the lancing unit is removable therefrom after use.

20. A method according to claim 16 further comprising sliding the lancing unit on the shell distally towards the physiological tissue to puncture the physiological tissue and sliding the lancing unit on the shell proximally from the physiological tissue to position the sensors near to the interrogation elements.

21. A method for analyzing a physiological fluid from a physiological tissue, comprising:

(a) installing a lancing unit into a shell such that it is removable therefrom after use, the lancing unit having a channel through a needle to a sharp point and having sensors positioned along the channel, the shell having interrogation elements corresponding to the sensors and a distal portion encircling the sharp point after installation, the interrogation elements being in direct communication with an analyzer;

(b) positioning the distal portion of the shell on the physiological tissue;

(c) sliding the lancing unit to extend the needle, pushing the sharp point from the shell to puncture the physiological tissue;

(d) conducting a physiological fluid from the physiological tissue from the sharp point up the channel;

(e) analyzing the physiological fluid at the sensors in the channel; and (f) sliding the lancing unit relative to the shell to retract the sharp point into the shell and position the sensors proximate to the interrogation elements to communicate information from the sensors to the interrogation elements and from the interrogation elements to the analyzer.

22. A method of making a device for analyzing a physiological fluid, comprising:

(a) forming a lancing unit with a channel extending from a portion of the lancing unit through a needle to a sharp point;

(b) immobilizing chemicals that interact with one or more constituents of the physiological fluid at one or more sensors along the channel;

(c) forming a shell in which the lancing unit can slide, the shell having interrogation elements corresponding to the sensors to which information from the sensors can be communicated thereto when the lancing unit is in the shell at a retracted state; and (d) installing the lancing unit in the shell wherein said interrogation elements are in communication with an analyzer.

* * * * *